US010889837B2

(12) United States Patent
Lewis et al.

(10) Patent No.: US 10,889,837 B2
(45) Date of Patent: Jan. 12, 2021

(54) CORN BLENDS THAT INCLUDE HIGH OIL CORN AND METHODS OF MAKING ONE OR MORE BIOCHEMICALS USING HIGH OIL CORN OR CORN BLENDS THAT INCLUDE HIGH OIL CORN

(71) Applicant: POET Research, Inc., Sioux Falls, SD (US)

(72) Inventors: Stephen M. Lewis, Sioux Falls, SD (US); John Kenneth Grearson, Sioux Falls, SD (US); Neelakantam V. Narendranath, Sioux Falls, SD (US); Francis Michael Swain, Tea, SD (US); Brett Yerdon, Sioux Falls, SD (US); Camille Kelly Nelson, Hartford, SD (US)

(73) Assignee: POET Research, Inc., Sioux Falls, SD (US)

( * ) Notice: Subject to any disclaimer, the term of this patent is extended or adjusted under 35 U.S.C. 154(b) by 291 days.

(21) Appl. No.: 14/951,111

(22) Filed: Nov. 24, 2015

(65) Prior Publication Data

US 2016/0145650 A1 May 26, 2016

Related U.S. Application Data

(60) Provisional application No. 62/083,668, filed on Nov. 24, 2014.

(51) Int. Cl.
*C12P 7/08* (2006.01)
*C12P 19/02* (2006.01)
*C08B 30/02* (2006.01)
*C12P 7/06* (2006.01)

(52) U.S. Cl.
CPC .............. *C12P 7/08* (2013.01); *C08B 30/02* (2013.01); *C12P 7/06* (2013.01); *C12P 19/02* (2013.01); *Y02E 50/10* (2013.01)

(58) Field of Classification Search
None
See application file for complete search history.

(56) References Cited

U.S. PATENT DOCUMENTS

| 6,639,132 | B1 | 10/2003 | Duvick et al. |
| 6,648,930 | B2 * | 11/2003 | Ulrich ............... A23D 9/00 44/308 |
| 6,703,227 | B2 | 3/2004 | Jakel et al. |
| 7,371,941 | B2 | 5/2008 | Pylman et al. |
| 7,378,579 | B2 | 5/2008 | Pylman et al. |
| 7,528,303 | B2 | 5/2009 | Pylman et al. |
| 7,842,484 | B2 | 11/2010 | Lewis |
| 7,919,291 | B2 | 4/2011 | Lewis et al. |
| 8,409,639 | B2 | 4/2013 | Lewis et al. |
| 8,409,640 | B2 | 4/2013 | Lewis et al. |
| 8,470,550 | B2 | 6/2013 | Lewis |
| 8,497,082 | B2 | 6/2013 | Lewis |
| 8,597,919 | B2 | 12/2013 | Lewis |
| 8,679,793 | B2 | 3/2014 | Lewis |
| 8,702,819 | B2 | 4/2014 | Bootsma |
| 8,748,141 | B2 | 6/2014 | Lewis et al. |
| 9,061,987 | B2 | 6/2015 | Bootsma |
| 2003/0194788 | A1 | 10/2003 | Jakel et al. |
| 2004/0234649 | A1 | 11/2004 | Lewis et al. |
| 2005/0233030 | A1 | 10/2005 | Lewis et al. |
| 2005/0239181 | A1 | 10/2005 | Lewis et al. |
| 2007/0022491 | A1 | 1/2007 | Pylman et al. |
| 2007/0022492 | A1 | 1/2007 | Pylman et al. |
| 2007/0178567 | A1 | 8/2007 | Lewis |
| 2009/0017164 | A1 * | 1/2009 | Schisler ............... C12P 7/06 426/62 |
| 2010/0260918 | A1 * | 10/2010 | Wang ............... A23K 10/38 426/601 |
| 2012/0137391 | A1 | 5/2012 | Davis et al. |
| 2013/0109873 | A1 | 5/2013 | Bootsma |
| 2013/0180016 | A1 | 7/2013 | Narva et al. |
| 2014/0186907 | A1 | 7/2014 | Bootsma |
| 2014/0283226 | A1 | 9/2014 | Lewis et al. |
| 2014/0366786 | A1 | 12/2014 | Carroll et al. |
| 2015/0037857 | A1 | 2/2015 | Redford |
| 2015/0197707 | A1 | 7/2015 | Redford |
| 2015/0291923 | A1 | 10/2015 | Bootsma |
| 2017/0051322 | A1 | 2/2017 | Bushong et al. |
| 2018/0235167 | A1 | 8/2018 | Lewis et al. |

FOREIGN PATENT DOCUMENTS

| WO | 2004/081193 A2 | 9/2004 |
| WO | 2011/163613 A1 | 12/2011 |
| WO | 2017/059083 A1 | 4/2017 |

OTHER PUBLICATIONS

Harakotr et al., "Anthocyanin, phenolics and antioxidant activity changes in purple waxy corn as affected by traditional cooking", Food Chemistry 164 (May 21, 2014) pp. 510-517.
Petroni et al., "Anthocyanins in corn: a wealth of genes for human health", Planta (Aug. 9, 2014) 240: pp. 901-911.
Li et al., "Antioxidative effect of purple corn extracts during storage of mayonnaise", Food Chemistry 152 (Dec. 1, 2013) pp. 592-596.
Pham Van Hung, "Phenolic compounds of cereals and their antioxidant capacity", Critical Reviews in Food Science and Nutrition (Jul. 30, 2014).
Dia et al., "Processing Method and Corn Cultivar Affected Anthocyanin Concentration from Dried Distillers Grains with Solubles", Journal of Agricultural and Food Chemistry, Mar. 11, 2015, 63, pp. 3205-3218.
International Search Report and Written Opinion from International Application No. PCT/US2015/062469, dated Apr. 4, 2016 (16 pages).

(Continued)

*Primary Examiner* — Emily A Cordas
(74) *Attorney, Agent, or Firm* — Kagan Binder, PLLC (57) ABSTRACT

The present invention relates to using high oil corn to make a biochemical such as ethanol. More particularly, the invention relates to methods of making a biochemical using relatively low temperature saccharification followed by fermentation or simultaneous saccharification and fermentation of high oil corn.

20 Claims, 4 Drawing Sheets

(56) References Cited

OTHER PUBLICATIONS

Shi et al., "Production and evaluation of biodiesel and bioethanol from high oil corn using three processing routes", Bioresource Technology 128 (Oct. 22, 2012) pp. 100-106.
Clausen, "Planting the Seed", Farm Country, The Country Today, Feb. 23, 2011 (1 page).
New Vision Co-op Newsletter, vol. 17, Issue 2, www.newvision.coop, Jun. 2015 (6 pages).
Haspel, "In defense of corn, the world's most important food crop", The Washington Post, Jul. 12, 2015 (4 pages).
"Monsanto Seeks Second Refuge-in-the-Bag Approval", IHS Chemical Week, Jun. 29, 2010 (2 pages).

* cited by examiner

CORN BLENDS THAT INCLUDE HIGH OIL CORN AND METHODS OF MAKING ONE OR MORE BIOCHEMICALS USING HIGH OIL CORN OR CORN BLENDS THAT INCLUDE HIGH OIL CORN

RELATED APPLICATION

The present non-provisional Application claims the benefit of commonly owned provisional Application having Ser. No. 62/083,668, filed on Nov. 24, 2014, which provisional Application is incorporated herein by reference in its entirety.

FIELD OF INVENTION

The present invention relates to using high oil corn grain to make a biochemical. More particularly, the invention relates to corn blends that include high oil corn, related methods of planting, and methods of making a biochemical using relatively low temperature saccharification or simultaneous saccharification and fermentation using high oil corn grain or corn grain blends that include high oil corn.

SUMMARY OF INVENTION

Embodiments of the present disclosure include a method of producing a biochemical from corn, the method including:

milling at least a portion of corn grain to provide corn starch and corn oil, wherein the corn grain includes corn grain having an average oil content of greater than 4.0 percent on a dry weight basis of the corn grain;

forming a first aqueous composition including the corn starch and the corn oil;

enzymatically hydrolyzing at least a portion of the starch in the first aqueous composition at a temperature of 40° C. or less to produce a second aqueous composition including glucose; and fermenting the second aqueous composition to produce a third aqueous composition including the biochemical, wherein the second composition includes a microorganism that can ferment the glucose into the biochemical.

Embodiments of the present disclosure also include a bag or container of a corn seed blend that includes:

a) #2 yellow dent corn grain having an average oil content of less than 4 percent on a dry weight basis of the corn grain; and b) at least 5% of corn grain having an average oil content of at least 13.5 percent on a dry weight basis of the corn grain.

Embodiments of the present disclosure also include a method of harvesting corn including:

a) planting seed blend that includes:
 i) #2 yellow dent corn grain having an average oil content of less than 4 percent on a dry weight basis of the corn grain; and
 ii) at least 5% of corn grain having an average oil content of at least 13.5 percent on a dry weight basis of the corn grain; and b) harvesting the corn plants produced from corn seed blend in step (a).

DETAILED DESCRIPTION

The present invention relates to methods of producing one or more biochemicals using high oil corn, or corn blends that include high oil corn. For illustration purposes, one or more exemplary embodiments are described below in the context of using yeast to produce ethanol via fermentation. However, the methods described herein can be used with other organisms such as bacteria and can be used to produce other biochemicals such as butanol, etc.

High Oil Corn Grain

With respect to oil content, high oil corn can have relatively higher corn oil content as compared to #2 yellow dent corn. As used herein, "high oil" corn refers to corn grain having an average corn oil content of greater than 4.0 percent on a dry weight basis of the corn grain. In some embodiments, high oil corn includes corn grain having an average corn oil content of at least 5.0 percent on a dry weight basis of the corn grain. In some embodiments, high oil corn includes corn grain having an average corn oil content of at least 5.5 percent on a dry weight basis of the corn grain. In some embodiments, high oil corn includes corn grain having an average corn oil content from 6 percent to 30 percent on a dry weight basis of the corn grain. In some embodiments, high oil corn includes corn grain having a corn oil content from 6 percent to 20 percent on a dry weight basis of the corn grain. In some embodiments, high oil corn includes corn grain having a corn oil content from 6 percent to 15 percent on a dry weight basis of the corn grain. In some embodiments, high oil corn includes corn grain having a corn oil content from 4.5 percent to less than 7 percent on a dry weight basis of the corn grain. The corn oil can include one or more fatty acids, especially fatty acids (e.g., oleic acid) that can be used by organisms such as yeast as nutrients during fermentation.

In some embodiments, high oil corn having an oil content that is not too high may advantageously provide benefits described herein of elevated levels oil as compared to #2 yellow dent corn, while at the same time reduce the viscosity that may be caused by high oil corn having very high levels of oil (e.g., 15% on a dry matter basis). Using high oil corn having an oil content within an appropriate range in a corn slurry during saccharification and/or fermentation may permit a higher solids level to be processed as compared to #2 yellow dent corn and very high oil corn grain. For example, a high oil corn having an oil content from greater than 4 percent to 10 percent, or even from greater than 4 to 7 percent on a dry weight basis of the corn grain may permit corn slurry (e.g., a corn mash) to have a solids content during saccharification and/or fermentation of greater than 37%, or even greater than 38%, such as from 40-50% solids.

High oil corn grain can also include water, starch, protein, enzymes (i.e., "endogenous" enzymes), pigments, antioxidants, nutraceuticals, and amino acids (e.g., essential amino acids for yeast growth and fermentation performance, as well as animal nutrition). With respect to starch content, high oil corn can have relatively lower starch content as compared to #2 yellow dent corn. In some embodiments, high oil corn includes corn grain having a starch content of 70 percent or less on a dry weight basis of the corn grain, 68 percent or less on a dry weight basis of the corn grain, or even 65 percent or less on a dry weight basis of the corn grain. In some embodiments, high oil corn includes corn grain having a starch content of less than 69 percent on a dry weight basis of the corn grain. In some embodiments, high oil corn includes corn grain having a starch content from 58 to 65 percent on a dry weight basis of the corn grain.

With respect to protein content, high oil corn can have relatively higher protein content as compared to #2 yellow dent corn. In some embodiments, high oil corn includes corn grain having a protein content of 7 to 13 percent on a dry weight basis of the corn grain.

With respect to amino acids, high oil corn can have a relatively higher content of essential amino acids as compared to #2 yellow dent corn. Amino acids present in high oil corn can include lysine, threonine, tryptophan, cysteine, methionine and the like.

With respect to endogenous enzymes, high oil corn can have a relatively higher content of one or more endogenous enzymes as compared to #2 yellow dent corn. Exemplary endogenous enzymes in high oil corn include protease, amylase, phytase, fiber degrading enzymes, and the like. As discussed below, one or more endogenous enzymes can be in their active form during a "BPX" saccharification and/or fermentation.

In some embodiments, a high oil corn can have the nutrient profile shown below in Table 1.

TABLE 1

| Nutrient | Percent dry weight of corn grain |
|---|---|
| Starch | 58-70 |
| Protein | 7-13 |
| Oil | 6-18 |

High oil corn grain can be harvested from any of several different types of corn plants. Exemplary types of corn plants include hybrids, inbreds, transgenic plants, genetically modified plants or a specific population of plants.

High oil corn grain is commercially available under the tradename Value Plus™ high oil corn from Brownseed Genetics, LLC, Bay City, Wis. Exemplary high oil corn grain is also described in U.S. Pat. No. 7,528,303 (Pylman et al.); U.S. Pat. No. 7,371,941 (Pylman et al.); and U.S. Pat. No. 7,378,579 (Pylman et al.); the entireties of which patents are incorporated herein by reference for all purposes.

Corn grain having an elevated total corn oil content can be identified by any of a number of methods known to those of ordinary skill in the art. For example, the oil content of grain can be determined using American Oil and Chemical Society Official Method, 5$^{th}$ edition, March 1998, ("AOCS method Ba 3-38"). AOCS method Ba 3-38 quantifies substances that are extracted by petroleum ether under conditions of the test. The oil content or concentration is the weight percentage of the oil with respect to the total weight of the grain sample. Oil content may be normalized and reported at any desired moisture basis. Another suitable method for identifying high oil corn grain involves using a near infrared (NIR) oil detector.

Methods for developing corn inbreds, hybrids, transgenic species and populations that generate corn plants producing grain having elevated oil concentrations are known and described in Lambert (Specialty Corn, CRC Press Inc., Boca Raton, Fla., pp. 123-145 (1994).

Preparation of Corn Grain for Saccharification

Corn grain can be prepared so that the starch is accessible by enzymes during enzymatic saccharification (discussed below). In some embodiments, corn grain can be dry milled (e.g., hammer milled) to produce whole ground corn having a medium-to-fine grind for use in saccharification and/or fermentation and/or distillation. In some embodiments, corn grain can be dry-fractionated to separate components of the corn grain (e.g., germ) from each other and then recombine two or more components (e.g., the endosperm and germ) for) for saccharification and/or fermentation and/or distillation.

Alternatively, the germ could be separated from the corn grain and not recombined with other corn components prior to the low temperature saccharification process described herein below. In such an embodiment, the combination of the low temperature saccharification can avoid starch gelatinization so as to reduce slurry viscosity and avoid oil from the germ so as to also reduce slurry viscosity. Advantageously, the solids content of the slurry may be increased during saccharification and/or fermentation. For example, removing corn germ prior to low temperature saccharification may permit a corn slurry (e.g., a corn mash) to have a solids content during saccharification and/or fermentation of greater than 37%, or even greater than 38%, such as from 40-50% solids.

In some embodiments, the corn grain can be ground so that a substantial portion, e.g., a majority, of the ground corn grain fits through a sieve with a 0.1-5.0 mm screen, or even a 0.1-0.5 mm screen. For example, in an embodiment, about 70% or more, of the ground corn can fit through a sieve with a 0.1-0.5 mm screen.

In some embodiments, corn can be prepared by milling at least a portion of corn grain to provide corn starch and corn oil. The corn grain includes corn grain having an oil content of greater than 4.0 percent on a dry weight basis of the corn grain. In some embodiments, all of the corn grain used in milling, saccharification, and fermentation has an oil content of greater than 4.0 percent on a dry weight basis of the corn grain.

In other embodiments, the corn grain used in milling, saccharification, and fermentation is a corn grain blend having an average oil content of greater than 4.0 percent on a dry weight basis of the corn grain. For example, the corn grain blend can include #2 yellow dent corn grain (e.g., having an oil content of 4.0% or less on a dry matter basis) and at least 5% corn grain having an oil content of at least 18.0 percent on a dry weight basis of the corn grain. As another example, the corn grain blend includes #2 yellow dent corn grain and at least 25% corn grain having an oil content of at least 7.0 percent on a dry weight basis of the corn grain. As used herein, "#2 yellow dent corn grain" has an average oil content of about 3.5% on a dry weight basis (e.g., a range from 3 to 4% on a dry weight (dry matter) basis).

A corn grain blend having an average oil content of greater than 4.0 percent on a dry weight basis of the corn grain can be provided by several techniques. According to one technique, a corn blend can be provided by planting a mix of different corn seeds in a field, harvesting the mix of corn grains, and then milling the mix of corn grains. An example of planting a mix of different corn seeds includes mixing in the field 25% by weight of corn grain having an oil content of at least 7.0 percent on a dry weight basis of the corn grain with 75% by weight of #2 yellow dent commodity corn to form a corn grain blend that is then planted, harvested, and milled. This technique is known as Sidekick™ planting method by Brownseed Genetics, LLC, Bay City, Wis.

Another example of planting a mix of different corn seeds includes providing bags or containers of a corn seed blend that includes #2 yellow dent corn grain having an oil content of 4.0 percent or less on a dry weight basis of the corn grain; and at least 5% (e.g., at least 20%) of corn grain having an oil content of at least 18.0 percent on a dry weight basis of the corn grain. The bags or containers can be emptied into a planting device and planted in a field. The corn plants produced can be harvested so as to provide a corresponding corn grain blend. Advantageously, the bag or container concept can be used as "RIB," which is short-hand for "refuge in a bag." Inclusion of high oil corn in RIB can provide farmers supporting biochemical production with the opportunity to plant a single-bag refuge solution for corn including refuge (non-Bt) seed that farmers can plant across their entire field. This means that farmers can avoid planting a separate, structured refuge for above or below ground pests. In corn farming, a refuge can be an integral component of insect resistance management. The refuge provides a shelter for insects susceptible to Bt technology so that any rare individual insects that survive after feeding on Bt corn can mate with susceptible insects and produce susceptible offspring. This preserves Bt technology that helps corn plants protect themselves from insect pests. Further, growers, whilst continuously seeking to optimize yield, meet refuge requirements, and manage weed control and pests, tend to produce corn with high variability that can impact ethanol production processes. Inclusion of a small percentage of high oil corn (as low as 20%, or even 5%) into a genetically modified unit of corn seeds that requires refuge, can have a measurable and unexpected impact on fermentation kinetics, ethanol conversion efficiency, corn oil quantitation, and quality of DDGS as a direct result of enhanced amino acids, and protein.

Another technique for providing a corn grain blend having an average oil content of at least 4.0 percent on a dry weight basis of the corn grain involves blending different corn grains at the mill from separate sources. For example, a first source of corn grain comprising #2 yellow dent corn grain and a second source of corn grain comprising corn grain having an oil content of at least 4.0 percent on a dry weight basis of the corn grain can be mixed at the mill to form a corn grain blend prior to grinding. A ground corn composition can be mixed with an appropriate amount of water to form an aqueous composition (e.g., a slurry) for subsequent saccharification of the starch and fermentation of glucose. In an embodiment, whole ground corn can be mixed with liquid at about 20 to about 50 wt-% or about 25 to about 45 wt-% dry whole ground corn. High oil corn can be processed at higher dry solids in low temperature processes, enabling increased throughput of DDGS and ethanol.

In some embodiments, the aqueous slurry includes at least a portion of the starch, endogenous enzymes, amino acids, and oil from the high oil corn because one or more of these components can be used by yeast (or converted into other components that can be used by yeast) during fermentation to enhance yeast performance. Preferably, the entire contents of the corn grain (e.g., starch, protein, oil, endogenous enzymes, amino acids, etc.) are included in the aqueous slurry that will be used for saccharification and fermentation because there are many nutrients in (or derived from) the entire corn grain that can be used by yeast during fermentation to enhance yeast performance. Any corn grain components (e.g., fiber, oil, etc.) remaining after fermentation are preferably extracted/separated after fermentation and/or distillation, as discussed below. For example, as mentioned the corn oil component can include one or more nutrients (e.g., oleic acid) for yeast. In addition, because starch constitutes the largest mass portion of the corn grain it can be more efficient to extract other components (e.g., oil, fiber, protein, etc.) after at least a portion of the starch has been removed (i.e., hydrolyzed into glucose, which is consumed by yeast).

In some embodiments, a biochemical such as ethanol can be toxic to yeast if the ethanol content is too high, which means that the corn solids content can be limited for a given fermentation batch. Advantageously, a relatively higher corn solids content (e.g., greater than 38% such as from 40-50% solids) can be processed with high oil corn as compared to #2 yellow dent corn, which can result in more DDGS produced for a given fermentation batch using high oil corn while maintaining the ethanol content due do the starch content in the high oil corn.

Saccharification

After forming an aqueous slurry that includes the corn material from preparing high oil corn as described above, the aqueous slurry can be subjected to enzymatic saccharification to break down (hydrolyze) at least a portion of the starch into glucose that can be used by yeast during fermentation.

In some embodiments, saccharification is performed at conditions that do not degrade one or more corn grain components to an undue degree. While it can be desirable to break down as much starch into glucose as possible, it can be desirable to not degrade one or more enzymes to an undue degree so that the one or more enzymes remain in their active form. For example, while not being bound by theory, it is believed that protease enzymes that are endogenous to the high oil corn at higher levels than in normal #2 yellow corn can degrade corn grain protein so as to increase the free amino nitrogen (FAN) content of the slurry so that the yeast can use the FAN during fermentation. FAN is a measure of the concentration of utilizable amino acids and relatively small peptides (e.g., one to three units) which can be used by yeast for yeast cell growth and fermentation.

Further, while not being bound by theory, it is believed that undesirable "Maillard Reactions" can occur if high temperature gelatinization and liquefaction techniques are used instead of relatively low temperature saccharification techniques described herein. The Maillard Reactions can consume FAN during the high temperature gelatinization and liquefaction. That is, an amino group can react with a carbonyl group of a sugar, thereby reducing the FAN content and reducing the sugar yield. It is believed that the relatively low temperature saccharification conditions described herein can avoid such temperature induced Maillard Reactions and provide increased levels of FAN and glucose in the aqueous slurry, which are effectively utilized by the yeast in fermentation.

High temperature gelatinization and liquefaction techniques can damage other components of the corn grain, rendering them less valuable for the ultimate end use or making it more difficult to recover and separate after saccharification and/or fermentation. For example, the valuable oil quality can be detrimentally impacted by the formation of increased undesirable free fatty acids.

Also, performing saccharification below starch gelatinization temperatures can avoid undue increases in slurry viscosity caused by starch gelatinization and thereby may permit a corn slurry (e.g., a corn mash) to have a solids content during saccharification and/or fermentation of greater than 37%, or even greater than 38%, such as from 40-50% solids.

In some embodiments, an aqueous slurry does not include any exogenous proteases and saccharification is performed at conditions that preserves the amount of the initial FAN from the corn grain while at the same time increasing the amount of FAN due to the endogenous protease breaking down corn protein into additional FAN during fermentation. When low temperature conversion processes are combined with high oil corn containing higher levels of endogenous enzymes, it is possible to achieve simultaneous proteolysis, amylolysis, etc. due only to the native endogenous enzymes. In some embodiments that do not include adding exogenous protease to the aqueous slurry, the free amino nitrogen (FAN) content of the aqueous slurry can be at least 75 parts per million, even 300 parts per million, increasing up to 800 ppm during the saccharification and/or fermentation process.

Yet another advantage of preserving the active form of one or more endogenous enzymes during saccharification and/or fermentation is that endogenous enzymes (e.g., amylase and protease enzymes) can reduce the cost of adding exogenous enzymes to break down the starch and/or proteins into materials that can be used by yeast.

The relatively low temperature saccharification process mentioned throughout this application involves enzymatically hydrolyzing at least a portion of the starch in the aqueous slurry at a temperature below starch gelatinization temperatures, so that saccharification occurs directly from the raw native insoluble starch to soluble glucose while bypassing conventional starch gelatinization conditions. Starch gelatinization temperatures are typically in a range of 57° C. to 93° C. depending on the starch source and polymer type. By saccharifying starch according to the low temperature protocol described herein, dextrinization of starch using conventional liquefaction techniques is not necessary. The low temperature saccharification methodology described herein refers to the process of converting starch to smaller polysaccharides and eventually to monosaccharides, such as glucose. Conventional saccharification uses liquefaction of gelatinized starch to create soluble dextrinized substrate which glucoamylase enzyme hydrolyzes to glucose. In the present method, saccharification refers to converting raw starch to glucose with one or more exongenous enzymes, e.g., glucoamylase and acid fungal amylase. Such enzymes are disclosed in U.S. Pat. No. 7,842,484 (Lewis) and U.S. Pat. No. 7,919,291 (Lewis et al.), wherein the entireties of said patents are incorporated herein by reference.

In one embodiment, saccharification includes enzymatically hydrolyzing at least a portion of the starch in the aqueous slurry at a temperature below 40° C. or less to produce a slurry that includes glucose. In some embodiments, enzymatic hydrolysis occurs at a temperature in the range of from 25° C. to 35° C. to produce a slurry that includes glucose.

The aqueous slurry can include one or more additional ingredients to facilitate hydrolyzing the starch into glucose. For example, the aqueous slurry can include one or more exogenous amylase enzymes to help convert the starch to glucose. Exemplary exogenous amylase enzymes include fungal acid amylase, glucoamylase, and mixtures thereof.

An example of low temperature enzymatic hydrolysis as mentioned herein is referred to herein as "BPX" and is described in U.S. Pat. No. 7,842,484 (Lewis) and U.S. Pat. No. 7,919,291 (Lewis et al.), wherein the entireties of said patents are incorporated herein by reference. One desirable feature of the low temperature process is that it allows starch to be removed by fermentation, and separation and recovery of valuable corn components after fermentation, without damaging any of the valuable oil, amino acids, or other components as occurs during higher temperature gelatinization and liquefaction processes.

Fermentation

The glucose that is generated from saccharification can be fermented into one or more biochemicals (e.g., butanol, ethanol, xylitol, and the like). Systems for producing more than one biochemical from the glucose can be integrated together or be separate. Fermenting can be effected by microorganisms such as fungi and bacteria. Exemplary microorganisms include ethanologens, butanologens, etc.

In some embodiments the microorganism includes yeast that can produce ethanol. Fermenting can include contacting an aqueous slurry including sugars derived from high oil corn with yeast under conditions suitable for growth of the yeast and production of ethanol.

Any of a variety of yeasts can be employed as the yeast starter in the present process. Suitable yeasts include any of a variety of commercially available yeasts, such as commercial strains of *Saccharomyces cerevisiae*. Suitable strains include "Fali" (Fleischmann's), Thermosac (Alltech), Ethanol Red (LeSafre), BioFerm AFT (North American Bioproducts), Lallemand/Mascoma, and the like.

Optionally, one or more components (e.g., yeast nutrients) can be included in the aqueous slurry that is to be fermented. As mentioned above, in some embodiments exogenous proteases are not included to increase the FAN content because the endogenous proteases can be sufficient to generate a desired FAN content. Optionally, in some embodiments other exogenous sources of nitrogen such as urea can be included if desired.

High oil corn has a starch content per bushel that is lower as compared to #2 yellow dent corn. The ethanol yield in terms of ethanol per bushel of corn can be lower for high oil corn because of its relatively lower starch content, but the residual starch after fermentation can be less for high oil corn as compared to #2 yellow dent corn. While not being bound by theory, Applicant believes that high oil corn includes relatively higher amounts of components that can contribute to improved yeast performance when whole ground high oil corn is used in saccharification and fermentation. For example, high oil corn can include higher amounts of one or more fatty acids (e.g., oleic acid) that can be used by yeast as a nutrient. As another example, high oil corn can include higher amounts of active protease enzymes that can break down corn grain protein into amino acids and increase the FAN content for yeast. Because the temperature of saccharification does not degrade these components to an undue degree, they are available to benefit the yeast.

In some embodiments, the residual starch after fermentation is can be 1 to 2% of the dry weight of the slurry. While not being bound by theory, it is believed that this is because of both the endogenous enzymes contributing to the breakdown of the starch and also due to improved utilization of the carbohydrate by the yeast due to the improved nutrition in high oil corn processed with the low temperature method. In this case, improved conversion and utilization results in lower starch and lower residual glucose relative to levels observed when processing normal #2 yellow corn. Fermentation efficiency can be improved to levels that are higher than expected based only on the starch content alone.

Residual starch can be measured by a variety of enzymatic methods, including that of Megazyme International, Wicklow, Ireland.

One advantage of having a lower starch content per bushel is that the ethanol content produced per bushel can be relatively lower as compared to #2 yellow dent corn such that a higher level of solids can be fermented before the ethanol becomes toxic to the yeast. Fermenting at a higher solids level can produce a relatively higher yield of DDGS. DDGS produced from high oil corn may also be enhanced in essential amino acids and other valuable components. Lysine, for example, can be very susceptible to degradation during higher temperature gelatinization and liquefaction processes.

In some embodiments, saccharification and fermentation can occur simultaneously in the same reactor (also referred to as simultaneous saccharification and fermentation (SSF)).

Recovering a Biochemical from the Beer

The product of the fermentation process is referred to herein as "beer". For example, fermenting corn produces "corn beer". A biochemical such as ethanol can be recovered from the fermentation mixture, from the beer, by any of a variety of known processes. For example, ethanol can be recovered by distillation.

Optional Oil Separation/Extraction/Recovery

Optionally, at least a portion of the oil from the high oil corn grain can be recovered as a co-product after fermentation and/or distillation and used in a variety of industrial applications, food grade nutritional uses, edible compositions and the like. The oil can be recovered by any of a variety of techniques known to those of skill in the art such as centrifugation, pH adjustment, solvent extraction, and the like. The corn oil is preferably separated after fermentation and/or distillation because as mentioned above, 1) at least a portion of oil can contribute to the nutrition of the yeast and 2) starch constitutes the largest mass portion of the corn grain so it can be more efficient to extract other components (e.g., oil, fiber, protein, etc.) after at least a portion of the starch has been removed (i.e., hydrolyzed into glucose, which is consumed by yeast). In some embodiments, using high oil corn can unexpectedly help reduce the caustic required to break an oil emulsion to recover the corn oil such that the average oil pH can be reduced by up to 1 pH unit less as compared to corn oil from 100% #2 commodity yellow dent corn.

EXAMPLE 1

To evaluate the processing of high oil corn at the plant scale, 81,239 bushels of SideKick™ (blend of 25% High oil corn and 75% #2 yellow dent, also referred to as "HOC blend") corn was processed in 61 fermenters. 70 fermenters of baseline #2YDC was also processed as a comparison. The objectives included evaluation of: fermentation performance of the HOC blend; Extreme High Gravity Fermentation performance of HOC blend; and impact to oil yield and DDGS composition when using HOC blend in relation to #2YDC.

This trial showed that there was only a slight ethanol yield drop from 2.69 gal/bu to 2.68 gal/bu from using the HOC blend when yeast genetically modified for reduced glycerol production in addition to gluco-amylase expression was used. HOC blend oil yield increased more than expected. With a constant oil recovery rate of 60%, oil yield was found to be increased by 31% from processing HOC blend (Table 2). Comparing oil composition in HOC blend to #2YDC, extracted oil yield was higher with HOC blend than expected suggesting the oil from HOC blend being more accessible for extraction. No substantial decrease in DDGS yield was detected, and residual starch levels were similar. Corn composition for this crop suggested less starch loss in the HOC blend than anticipated and lower protein than #2YDC suggesting the HOC blend may trade oil for protein and not just starch (Table 3). This decrease in protein carried through into the DDGS composition which showed lower protein amounts and higher oil amounts for DDGS from HOC blend runs (Table 4). This higher oil in the DDGS is in addition to the additional oil that was extracted from the corn oil extraction process.

TABLE 2

Oil and Ethanol yield

| Corn type | Oil Yield (lb/bu) | Ethanol Yield (gal/bu) |
|---|---|---|
| HOC blend | 1.33 | 2.68 |
| 2YDC | 1.01 | 2.69 |

TABLE 3

Corn composition

| Corn type | Protein (DMB) | Oil (DMB) | Starch (DMB) |
|---|---|---|---|
| HOC blend | 6.58 | 4.47 | 73.86 |
| 2YDC | 7.11 | 3.76 | 74.84 |

TABLE 4

DDGS composition

| Corn type | Protein (0% MB) | Oil (0% MB) | Fiber (0% MB) |
|---|---|---|---|
| HOC blend | 26.4 | 19.4 | 5.4 |
| 2YDC | 28.5 | 16.4 | 5.5 |

EXAMPLE 2

Fermentations were carried out in 500 mL bottles with 300 mL corn mash. The corn mash was prepared using various blends of #2 yellow dent corn with an average oil content of 3.79% (DMB) and high oil corn having an average oil content of 10.78% (DMB) by weight on a dry matter basis (referred to as "HOC" or "high oil corn") from Brownseed Genetics, Bay City, Wis. in reverse osmosis water at 34% fill solids. Both the #2 yellow dent and high oil corn samples were ground in a lab hammer mill from Perten Instruments using a 2 mm screen to give a grind size equivalent to the grind size obtained at any commercial biorefinery practicing the BPX process. The high oil corn was blended in with #2 yellow dent corn, in triplicate, at the following inclusion rates: 0%, 5%, 10%, 15%, 20%, 25%, 50%, 75%, and 100% on a dry weight matter basis. Both #2 yellow corn flour and high oil corn flour were weighed into each fermentor. The corn flour and water slurries in each fermentor were pH adjusted to 4.8 using 10% v/v sulfuric acid. Lactoside247™ (from Lallemand Biofuels & Distilled Spirits, Duluth, Ga.) and urea were added at 2.6 ppm and 500 ppm, respectively. Then, the BPX enzyme blend was added at a dose rate of 180 L for a 550,000 gal fermentor. This is equivalent to 0.0151 FAU-F/g dry corn solids and 0.1585 AGU/g dry corn solids for the alpha amylase and glucoamylase dose, respectively. After mixing the contents thoroughly, yeast grown in a yeast prop reactor (described below) was added to the fermentors at a 5% w/v inoculation rate. The contents of each fermentor post yeast addition was mixed well and the bottles were placed in a circulating water bath set at 32.8° C. (91° F.). The temperature was staged during the entire course of fermentation as follows: 32.8° C. for 0-16 hrs; 32.2° C. for 16-24 hrs; 31.1° C. for 24-48 hrs; and 30.6° C. for 48-88 hrs. After 23.5 hours of yeast addition, 21.5 mL of reverse osmosis water was added to each fermenter and stirred. Samples were withdrawn at 24, 48, 72, and 88 hours for sugars, organic acids, and alcohol analysis. The 88 hour drop samples were analyzed for residual solids, starch, protein and oil.

Yeast propagation: a strain of *S. cerevisiae* engineered both for the production of glucoamylase and reduction in glycerol production was used. The yeast inoculum was prepared in a corn mash based yeast prop. The #2 yellow dent corn flour was mixed with reverse osmosis water to obtain a 35% solids slurry. Lactoside247™ and urea were added at 5.2 ppm and 1000 ppm, respectively. The enzyme was added at 7.7 L per 20,000 gal tank. This is equivalent to 0.0172 FAU-F/g dry corn solids and 0.1803 AGU/g dry corn solids for the alpha amylase and glucoamylase dose, respectively. To this mix, cream yeast formulation was added for an equivalent dose of 0.6 g dry yeast/L of mash. The yeast prop reactor was placed in a water bath shaker set at 32.2° C. (90° F.), shaking at 150 rpm for 8 h after which appropriate quantities from the yeast prop were added to the fermentor bottles as described above.

Figure 2:
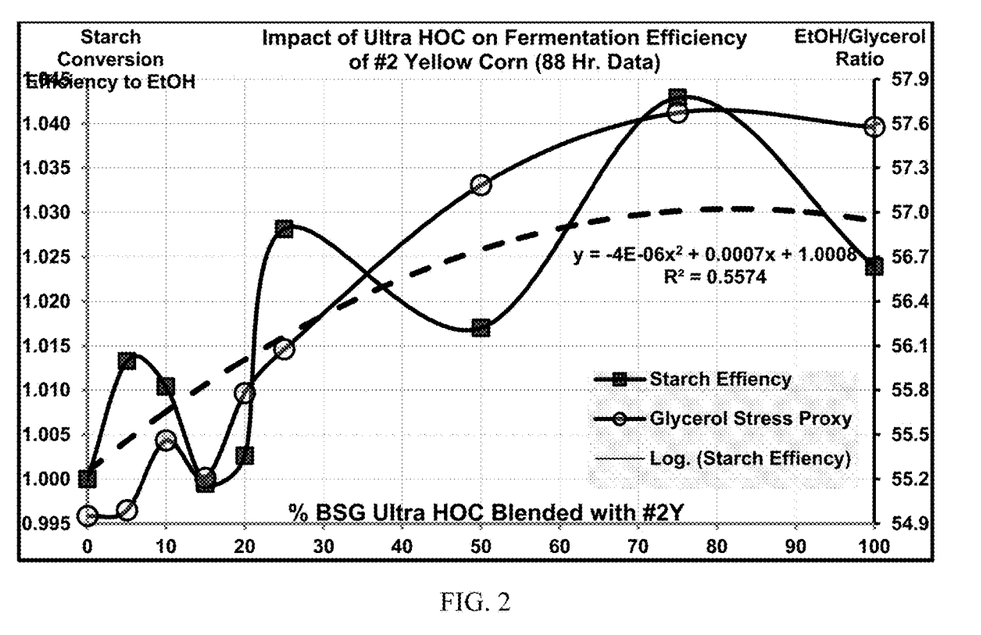
FIG. 2 shows starch conversion efficiency and ethanol:glycerol ratio as a proxy indicating yeast stress from the Example 2.
Figure 4:
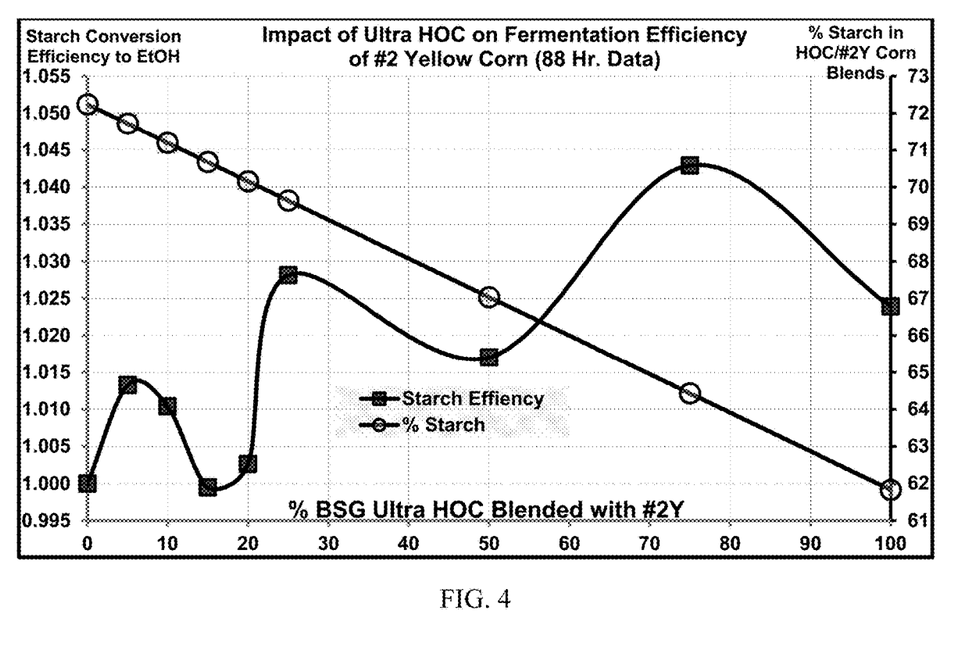
FIG. 4 shows starch conversion efficiency and % starch on dry basis as influenced by the various blends of #2 yellow dent corn and high oil corn from the Example 2.

Results:

FIGS. 2 & 4 refer to fermentation efficiency or starch conversion efficiency. The ratio of ethanol to glycerol is also a proxy for yeast stress, and this is shown in FIG. 2. FIG. 2, in other words, shows both fermentation (starch conversion) efficiency and the yeast stress proxy, while FIG. 4 shows only fermentation (starch conversion) efficiency, but it shows it in direct relation to the changing starch content on the Y-axis.

Figure 3:
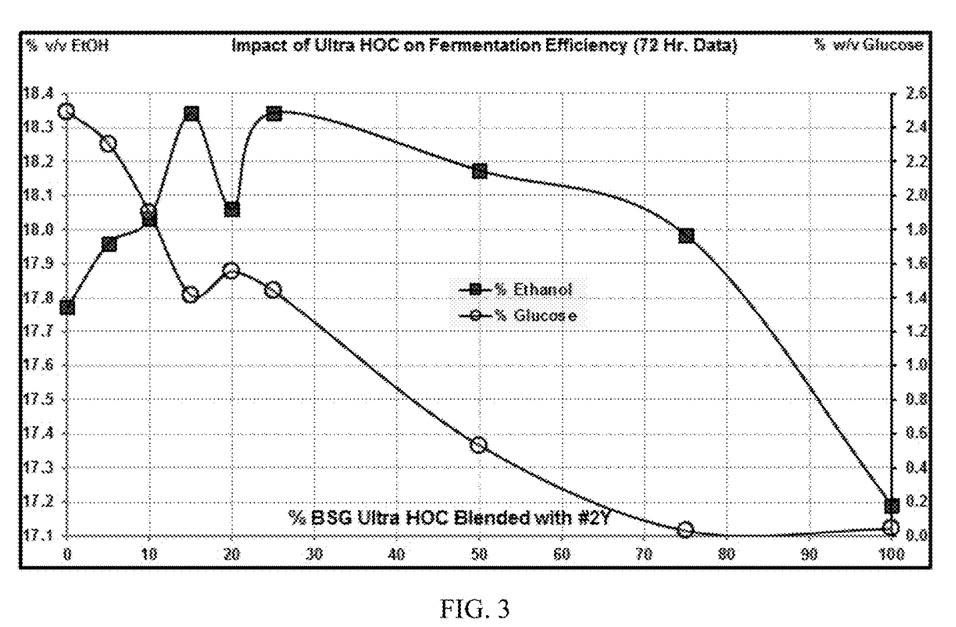
FIG. 3 shows ethanol and glucose data at drop from the Example 2.
Figure 7:
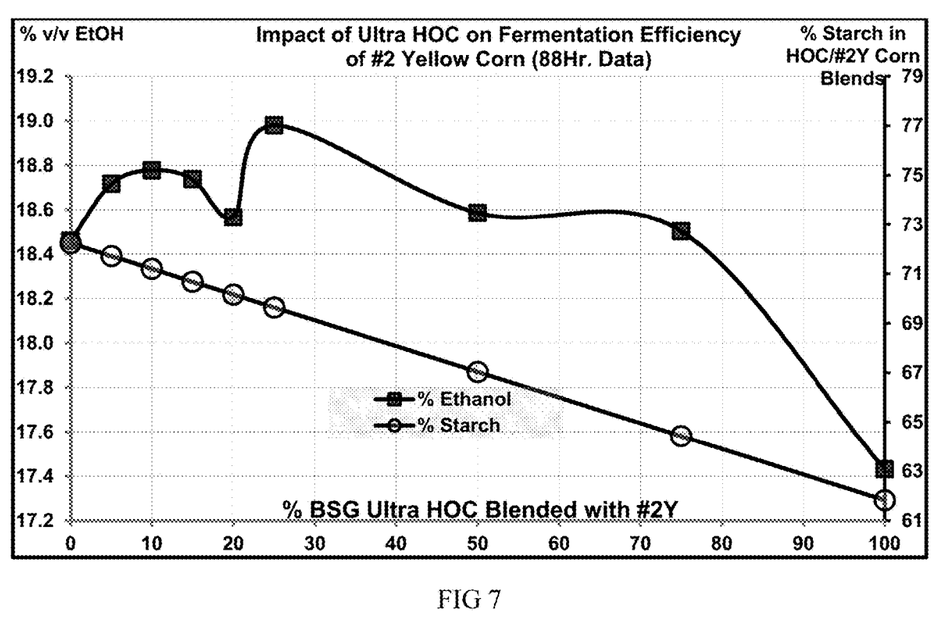
FIG. 7 shows drop ethanol titers at 88 hour and % starch on dry basis as influenced by various blends of #2 yellow dent corn and high oil corn from Example 2

Starch Conversion Efficiency: High Oil Corn (HOC) from Brownseed Genetics contains higher levels of endogenous enzymes and free amino nitrogen (FAN) which is believed to stimulate yeast growth and fermentation. As described below, the data shows that for a given starch content, the HOC starch is more highly fermentable than #2 yellow dent corn. While not being bound by theory it is believed that this is partly due to a change in starch structure to that of more amylopectin starch, and also due to the enhanced nutritional content of HOC. As HOC is blended with #2 yellow dent corn in increasing amounts, while maintaining the same dry solids corn, and fermented as described above, the data in FIG. 4 shows a trend toward improved starch conversion efficiency when the ethanol titer achieved is compared to the original starch present in the fermentation. The starch conversion efficiency is calculated by indexing the amount of ethanol produced per unit of starch present in original corn. The left axis of FIG. 4 shows the amount of starch found in inbound corn, while the right axis shows the conversions indexed to fermentations involving 100% 2YDC. Additionally, FIG. 2 shows the same increase in starch conversion efficiency and a logarithmic equation of starch efficiency. Because the starch conversion efficiency in HOC is greater than commodity #2 yellow corn, the ethanol yield does not drop as much as predicted based on the starch content alone, as shown in FIG. 7, which is the relationship between starch content in blends and ethanol titer/yield. FIG. 7 shows ethanol yield for HOC blends is higher than that for 2YDC for all blends below 75% HOC inclusion. It also shows that as the HOC inclusion increases the overall starch content in the blends decreases. Eventually, the starch content drops so low that the ethanol content also decreases below that of #2 yellow corn (results show ETOH titer decreases after 75% HOC inclusion). In FIG. 3, shown where the starch conversion efficiency of the HOC/#2Y blends are compared, the residual glucose in the fermentations was converted to equivalent ethanol using a standard mass balance of 0.511 grams of ethanol per gram of glucose, and a fermentation efficiency of 95%. The enhanced fermentation efficiency of starch is shown in FIG. 3.

Figure 1:
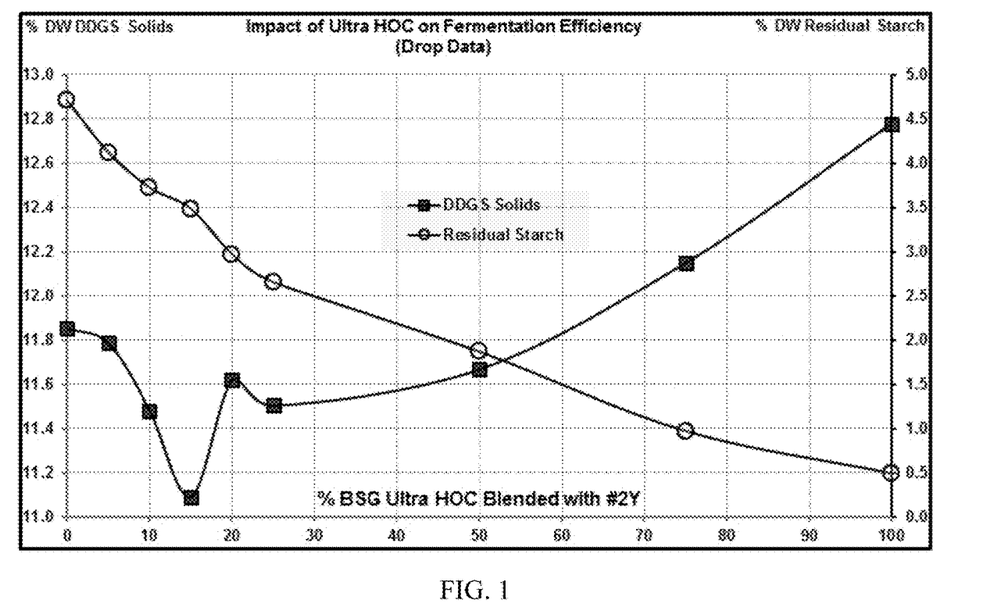
FIG. 1 shows DDGS solids and residual starch data from the Example 2.

The improvement in starch conversion efficiency is also shown in the residual starch contents for the series of fermentations described above. In FIG. 1, comparing dry weight of final fermentation solids and dry weight residual starch, the impact of increased high oil corn (HOC) can be observed. As HOC is blended with #2YDC corn, fermentation efficiency increases initially, and drop solids (which eventually become DDGS) decreases. Residual starch decreases throughout the range examined. Eventually however, solids begin to increase at HOC blend levels above ~50%, and the ethanol yield per weight of HOC decreases as the make up of the solids would become less starch, and more of the other components. These other components are not fermented, and carried through to the DDGS.

It should be noted that in the series of experiments shown, blending HOC with #2 yellow corn is very similar in effect to the case of planting HOC with varying percentages of #2 yellow corn using the previously described Sidekick™ planting method. In terms of achieving a desired fermentation effect, Examples 1 and 2 show that the effect can be achieved by either blending HOC corn with #2 yellow dent corn at the ethanol plant at desired percentage blend rates, or by planting HOC with #2 yellow dent corn according to the Sidekick™ planting method, which was the method used in Example 1.

Figure 5:
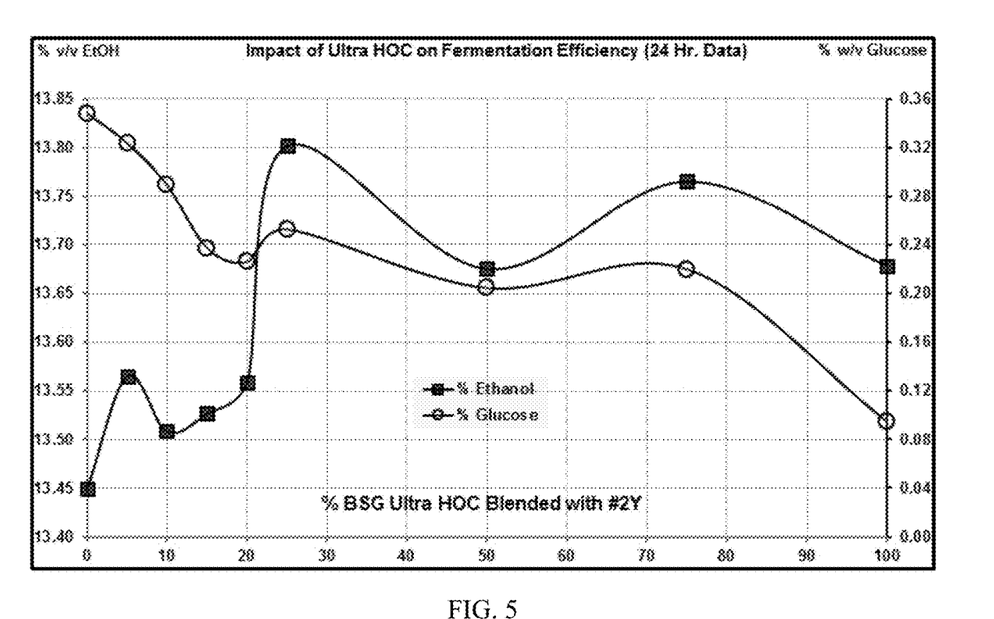
FIG. 5 shows ethanol and glucose 24 hour data from the Example 2.
Figure 6:
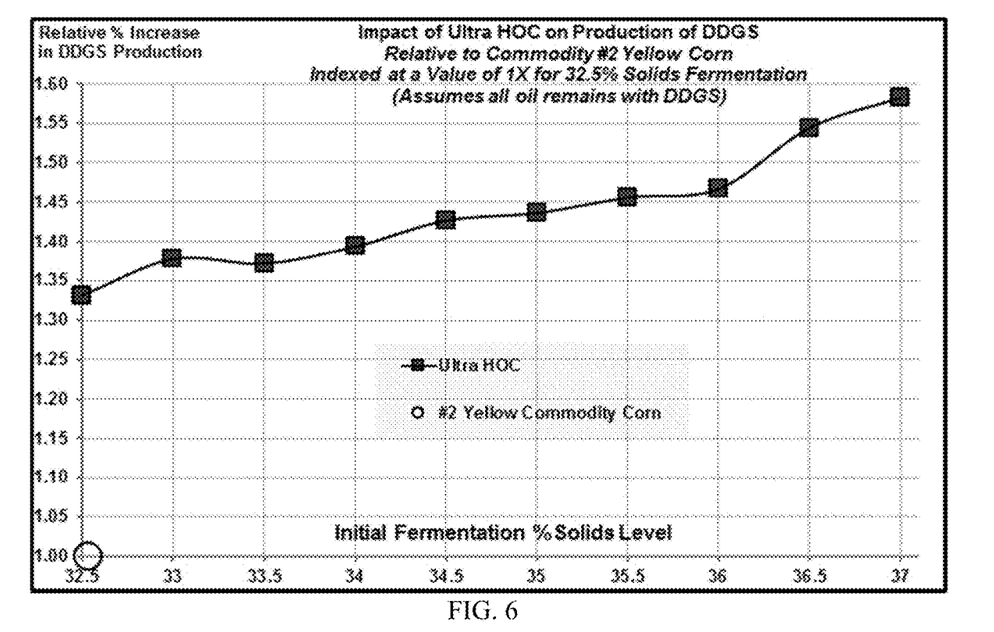
FIG. 6 shows DDGS data from the Example 2.

Ethanol Fermentation Rate: The impact of improvements in yeast nutrition and starch conversion efficiency can also be seen in the rate of ethanol fermentation with increasing levels of HOC corn. This can be seen when examining the amount of ethanol produced early in fermentation. Despite the decreased starch content of HOC corn, fermentations containing increasing amount of HOC are faster at 24 hours than they are with #2 yellow commodity corn alone, as shown in FIG. 5. The change in fermentation rate is significant and unexpected, especially when you consider the reduced starch in the HOC. As starch is reduced, we would expect the rate to decrease, but we see the opposite effect with HOC early in fermentation.

Ethanol/Glycerol Ratio: The production of glycerol in corn based ethanol fermentations can be used an indication for the amount of stress the yeast is exposed to during the course of fermentation. As ethanol increases throughout fermentation, glycerol can increase, partly in response to the increasing stress which higher levels of ethanol impart to the yeast cells. As shown in FIG. 2 as starch conversion efficiency improves, the amount of ethanol formed is higher for a given amount of glycerol produced. These two trends show that as the level of HOC increases, the glucose resulting from the conversion of the starch is converted more efficiently to ethanol than glycerol, resulting in a higher ethanol/glycerol ratio. While not being bound by theory, it is believed that the nutrition of the corn based medium is superior in the case of increasing levels of HOC, thereby causing the stress related glycerol levels to not rise as much as one might expect relative to the increasing ethanol content.

Energy per Acre: The benefit of using corn for ethanol production is readily recognized. Nutritionally, it has one of the highest calorie outputs per acre relative to other grains and oilseeds. In the case of HOC, the energy content per acre of cropland utilized is enhanced even further over commodity #2 yellow dent corn, making HOC one of the best options available for enhancing energy production per acre of cropland in an economical manner. Although other crops like rice may provide similar amounts of calories per acre relative to #2 yellow corn, on a price-to-calorie metric, corn is cheaper than rice, and HOC may be even more desirable than #2 yellow corn. If the goal is enhanced production of biofuels and nutritional calories, HOC can provide a good option for meeting the needs of both food and fuel. One measure of assessing whether a crop is a viable source of ethanol and animal feed production is energy production per acre. This measures the estimated amount of energy extracted from an acre of crop harvested. Soybeans, for example, can provide less calories on an acreage basis and can be very expensive on a caloric basis. Corn can also be more nutritionally complementary than soybeans because of its more favorable amino acid composition.

If we utilize the agricultural metric of calories produced per acre of cropland, #2 yellow corn is superior to other alternative crops in the US. In addition to calories, vitamins, minerals, fats and desirable protein can be important. In the case of each of these nutrients, the example of HOC improves the calorie argument for corn even further.

| Sample Name | Corn Composition | | | | Energy Values |
|---|---|---|---|---|---|
| | Yield (bu/acre) | Protein % DMB | Starch % DMB | Fat % DMB | Energy per Acre (Mcal) |
| #2 YC | 220 | 8.0 | 72.2 | 3.8 | 17,032 |
| Sidekick ™ | 220 | 9.0 | 70.5 | 5.1 | 17,496 |
| HOC at Yield Parity with #2YC | 220 | 9.4 | 61.8 | 10.8 | 18,479 |
| HOC and #2 Yield | 205 | 9.4 | 61.8 | 10.8 | 17,222 |

Assumptions in table:
Corn Composition from 2015 crop
Energy assumptions 4 kcal/g for starch, 4.2 kcal/g for protein, and 9.45 kcal/g of oil.
All % values are on dry matter basis.
1 bu of corn at 15% moisture is 56 lb.
Assumed yield parity at 220 bu/acre. (Corn genetics in HOC moving toward yield parity.)

An additional advantage of using HOC is the energy left in the remaining co-products. In the fermentation process, 49% of the starch can be converted to carbon dioxide. If this carbon dioxide is not captured, the equivalent starch energy can be lost to the atmosphere. Because the HOC has more protein and oil, the energy is retained through the process and ends up in the Co-Products.

| Sample Name | Loss of Energy from CO2 in Fermentation (Mcal/Acre) | Energy Remaining in Co-Products (Mcal/Acre) |
|---|---|---|
| Sidekick | 2,691 | 4,759 |
| #2 YC | 2,757 | 3,981 |
| HOC at Yield Parity with #2YC HOC and 93% #2 Yield | 2,198 | 6,818 |

Assumptions in table:
Corn composition as listed in the above table
Assume 95% fermentation efficiency from starch in corn.
1 bu of corn at 15% moisture is 56 lb.
Assumed yield parity at 220 bu/acre. (Corn genetics in HOC moving toward yield parity.)

| Corn Blends | Energy (Mcal/bushel) | Corn Composition Assumptions | | |
|---|---|---|---|---|
| | | Protein % DMB | Starch % DMB | Fat % DMB |
| #2 YC | 77.0 | 8.0 | 72.2 | 3.8 |
| 13.5% Oil | 77.5 | 9.4 | 59.1 | 13.5 |
| 15.0% Oil | 77.6 | 9.4 | 57.6 | 15.0 |
| 18.0% Oil | 77.8 | 9.4 | 54.6 | 18.0 |

*Energy value per bushel of corn for blends of 5% inclusion of HOC blends compared to #2YDC Assumptions in table:
Corn composition as listed in the above table
1 bu of corn at 15% moisture is 56 lb.
Assumed that as oil content increased, it traded for starch.

DDGS throughput: A potential advantage of higher levels of HOC corn is the previously mentioned increased oil yield per bushel of corn processed. This is potentially advantageous if the oil is used for biodiesel production, animal feed, or human food. The lower starch content can be utilized advantageously under certain economic conditions. The price of DDGS in the marketplace can be determined by many factors, including export demand and pricing of competing feeds in the domestic market. As a result, DDGS can sell at a higher or lower price than corn depending upon competing market factors. When DDGS returns are favorable, and DDGS sells for higher prices than #2 yellow dent corn, the lower starch content of HOC can be used to its advantage because HOC can enable higher solids processing with the BPX method of conversion. Solids can be increased in fermentation without experiencing viscosity limited corn throughput effect. As fermentation solids are increased, the resulting DDGS production can be increased. HOC, because if its superior starch conversion efficiency, ethanol production efficiency, and nutritional quality, enables higher solids processing using the BPX method without as significant a decrease in ethanol production efficiency. The decrease in efficiency as fermentation solids are increased is typically accompanied by increasing levels of residual glucose. These issues can be mitigated with HOC processing using the BPX method, since the BPX method can maintain the desirable attributes of HOC better than conventional processing. As a result, DDGS production can be increased significantly without experiencing decreased processing efficiencies. The impact of increasing fermentation solids on DDGS production throughput can be visualized by comparing increasing solids fermentations of HOC with #2 yellow fermentations indexed at 32.5% solids. Using the same fermentation solids of 32.5% for both HOC & #2 yellow corn illustrates that DDGS production is ~30% higher with HOC. Fermentation solids can be increased with HOC using the BPX method, not only because of the avoidance of viscosity related issues with the BPX process, but also because of the beneficial fermentation attributes of HOC grain. If we compare 37% solids HOC fermentations with 32.5% #2 Yellow fermentations, DDGS output is shown to increase by more than 50%. Enhanced production of DDGS from HOC is possible. In EXAMPLE 2, no oil has been recovered from the stillage added to the DDG to make DDGS.

What is claimed is:

1. A method of producing a biochemical and corn oil from corn, the method comprising:
   milling a whole corn grain blend to provide a feedstock comprising corn starch and corn oil, wherein the whole corn grain blend comprises a corn grain blend having an average oil content of greater than 4 percent on a dry weight basis of the corn grain blend, wherein the corn grain blend comprises a first corn grain having an oil content of 4 percent or less on a dry weight basis and a second corn grain having an oil content of at least 6 percent on a dry weight basis; wherein the first corn grain comprises #2 yellow dent corn grain and the second corn grain comprises an amount of at least 5 percent of the corn grain blend;
   adding water to at least a portion of the feedstock to form a first aqueous composition comprising corn starch and corn oil;
   enzymatically hydrolyzing at least a portion of the starch in the first aqueous composition to produce a second aqueous composition comprising glucose and corn oil;
   fermenting the second aqueous composition to produce a third aqueous composition comprising the biochemical and corn oil, wherein the second composition comprises a microorganism that can ferment the glucose into the biochemical; and
   recovering biochemical and corn oil after fermentation.

2. The method of claim 1, wherein the second corn grain has an oil content of at least 18 percent on a dry weight basis of the second corn grain.

3. The method of claim 1, wherein the second corn grain has an oil content of at least 7 percent on a-dry weight basis of the second corn grain and is present in an amount of at least 25 percent of the corn grain blend.

4. The method of claim 3, wherein the #2 yellow dent corn grain has an oil content of less than 4 percent on a dry weight basis of the corn grain.

5. The method of claim 1, further comprising, prior to milling:
   providing a first source of #2 yellow dent corn grain as the first corn grain;
   providing second source of the second corn grain having an oil content of at least 6 percent on a dry weight basis of the corn grain; and
   mixing the corn grain comprising #2 yellow dent corn grain and the second corn grain to form the corn grain blend having an average oil content of greater than 4 percent on a dry weight basis of the corn grain.

6. The method of claim 1, wherein the first aqueous composition further comprises one or more exogenous amylase enzymes to convert the starch to glucose.

7. The method of claim 6, wherein the one or more exogenous amylase enzymes comprises at least a fungal acid amylase and a glucoamylase.

8. The method of claim 1, wherein the recovering is at an average pH that is up to 1 pH unit less as compared to corn oil produced from 100 percent #2 yellow dent corn.

9. The method of claim 1, further comprising distilling at least a portion of the third aqueous composition to produce a fourth aqueous composition, wherein the fourth aqueous composition comprises at least a portion of the oil from the corn grain blend and further comprising separating at least a portion of the oil from the fourth aqueous composition, wherein the separating is at an average pH that is up to 1 pH unit less as compared to corn oil produced from 100 percent #2 yellow dent corn.

10. The method of claim 1, wherein the corn grain blend comprises one or more endogenous enzymes, and wherein the first aqueous composition comprises at least one of the endogenous enzymes in active form.

11. The method of claim 10, wherein the one or more endogenous enzymes comprises a protease in active form.

12. The method of claim 11, wherein the second aqueous composition does not include exogenous protease enzymes and the second aqueous composition comprises a free amino nitrogen (FAN) content of at least 75 parts per million.

13. The method of claim 1, wherein fermenting comprises a batch fermentation process, and wherein the second aqueous composition has a solids content greater than 38 percent.

14. The method of claim 1, wherein the second corn grain has a corn oil content of from 6 percent to 20 percent on a dry weight basis of the second corn grain.

15. The method of claim 1, wherein the biochemical comprises ethanol.

16. The method of claim 1, wherein enzymatically hydrolyzing at least a portion of the starch in the first aqueous composition is performed at a temperature of 40° C. or less.

17. The method of claim 1, wherein the second corn grain has an oil content of at least 18 percent on a dry weight basis of the second corn grain and is present in an amount of at least 20 percent of the corn grain blend.

18. The method of claim 1, wherein the second corn grain has a corn oil content of from 6 percent to 30 percent on a dry weight basis of the second corn grain.

19. A method of producing a biochemical and corn oil from corn, the method comprising:
   milling a whole corn grain blend to provide a feedstock comprising corn starch and corn oil, wherein the corn grain blend comprises a first corn grain having an oil content of 4 percent or less on a dry weight basis and a second corn grain having an oil content of at least 6 percent on a dry weight basis and present in an amount of at least 25 percent of the corn grain blend, wherein the first corn grain comprises #2 yellow dent corn grain;
   adding water to at least a portion of the feedstock to form a first aqueous composition comprising corn starch and corn oil;
   enzymatically hydrolyzing at least a portion of the starch in the first aqueous composition to produce a second aqueous composition comprising glucose and corn oil;
   fermenting the second aqueous composition to produce a third aqueous composition comprising the biochemical and corn oil, wherein the second composition comprises a microorganism that can ferment the glucose into the biochemical; and
   recovering biochemical and corn oil after fermentation.

20. The method of claim 19, wherein the corn grain blend comprises an average oil content of greater than 4 percent on a dry weight basis of the corn grain blend.

* * * * *